United States Patent
Uveborn

(10) Patent No.: US 8,979,813 B2
(45) Date of Patent: Mar. 17, 2015

(54) OSTOMY DEVICE

(75) Inventor: Johan Uveborn, Askim (SE)

(73) Assignee: Mölnlycke Health Care AB, Göteborg (SE)

(*) Notice: Subject to any disclaimer, the term of this patent is extended or adjusted under 35 U.S.C. 154(b) by 93 days.

(21) Appl. No.: 13/640,409

(22) PCT Filed: Apr. 8, 2011

(86) PCT No.: PCT/SE2011/050431
§ 371 (c)(1),
(2), (4) Date: Dec. 21, 2012

(87) PCT Pub. No.: WO2011/129749
PCT Pub. Date: Oct. 20, 2011

(65) Prior Publication Data
US 2013/0090617 A1  Apr. 11, 2013

Related U.S. Application Data

(60) Provisional application No. 61/322,973, filed on Apr. 12, 2010.

(30) Foreign Application Priority Data

Apr. 12, 2010  (SE) ...................................... 1050358

(51) Int. Cl.
*A61F 5/443* (2006.01)
*A61F 5/445* (2006.01)
(Continued)

(52) U.S. Cl.
CPC ....... *A61F 5/443* (2013.01); *A61F 2013/00817* (2013.01); *A61F 13/023* (2013.01);
(Continued)

(58) Field of Classification Search
CPC ......... A61F 5/443; A61F 5/445; A61F 5/448; A61F 5/451; A61F 13/02; A61F 2013/008; A61F 2013/00804; A61F 2013/00808; A61F 2013/00812; A61F 2013/00817; A61F 2013/00821; A61F 2013/00829; A61F 2013/00978; A61F 13/023; A61F 13/0236; A61F 13/024; A61F 2013/00412; A61F 2013/00421; A61F 2013/00476; A61F 2013/00795; A61F 13/063; A61F 2013/00182; A61F 2013/00289; A61F 2013/00868; A61M 1/0088; A61M 2001/0088; B31D 1/021; G09F 2003/0222; G09F 3/00; G11B 23/38; G11B 23/40

See application file for complete search history.

(56) References Cited

U.S. PATENT DOCUMENTS 2,233,209 A  2/1941 Herzog ......................... 128/156
3,292,626 A * 12/1966 Schneider ..................... 604/347
(Continued)

FOREIGN PATENT DOCUMENTS

CN  20118009311  4/2011
EP  0259184  3/1988
(Continued)

OTHER PUBLICATIONS

International Preliminary Report on Patentability issued on Oct. 16, 2012 for International Patent Application No. PCT/SE2011/050431, which was filed on Apr. 8, 2011 [Inventor—Uveborn; Applicant—Mölnlycke Health Care AB;] [7 pages].
(Continued)

*Primary Examiner* — Adam Marcetich
(74) *Attorney, Agent, or Firm* — Ballard Spahr LLP

(57) ABSTRACT

A body attachment wafer for an ostomy device is provided, which body attachment wafer has a stoma opening, and an adhesive layer. The adhesive layer is covered by a release layer, having an opening which corresponds to the stoma opening. The release layer is divided along at least one dividing line from the stoma opening to the periphery of the body attachment wafer, and the release sheet includes a first grip tab extending from the release sheet in the area of the at least one dividing line. The first grip tab is arranged to overlap the release sheet on the other side of the dividing line.

13 Claims, 2 Drawing Sheets

(51) Int. Cl.
*A61F 13/02* (2006.01)
*A61F 13/00* (2006.01)
*G09F 3/00* (2006.01)
*B31D 1/02* (2006.01)
*G09F 3/02* (2006.01)

(52) U.S. Cl.
CPC .............. *A61F2013/00821* (2013.01); *A61F 2013/00289* (2013.01); *A61F 13/0236* (2013.01); *A61F 2013/00412* (2013.01); *G09F 3/00* (2013.01); *B31D 1/021* (2013.01); *A61F 2013/00795* (2013.01); *A61F 13/024* (2013.01); *G09F 2003/0222* (2013.01)
USPC ........... 604/344; 604/332; 604/337; 604/338; 604/355; 604/327

(56) References Cited

U.S. PATENT DOCUMENTS

| | | | | |
|---|---|---|---|---|
| 3,683,918 A * | 8/1972 | Pizzella | .......... | 604/355 |
| 3,897,780 A * | 8/1975 | Trousil | .......... | 604/344 |
| 3,931,819 A * | 1/1976 | Weedle | .......... | 604/344 |
| 4,212,296 A * | 7/1980 | Schaar | .......... | 602/42 |
| 4,359,051 A * | 11/1982 | Oczkowski | .......... | 604/344 |
| 4,401,125 A * | 8/1983 | Taylor et al. | .......... | 600/528 |
| 4,445,898 A | 5/1984 | Jensen | .......... | 604/337 |
| 5,015,244 A | 5/1991 | Cross | .......... | 604/344 |
| 5,092,323 A * | 3/1992 | Riedel et al. | .......... | 602/54 |
| 5,242,381 A * | 9/1993 | Hoffmann et al. | .......... | 602/57 |
| 5,733,251 A * | 3/1998 | Johns | .......... | 602/57 |
| 5,891,076 A | 4/1999 | Fabo | .......... | 602/52 |
| 6,081,501 A * | 6/2000 | Hunter et al. | .......... | 720/720 |
| 6,607,799 B1 * | 8/2003 | Heinecke et al. | .......... | 428/40.1 |
| 6,841,716 B1 * | 1/2005 | Tsutsumi | .......... | 602/57 |
| 7,135,606 B1 * | 11/2006 | Dozier et al. | .......... | 602/57 |
| 2001/0027285 A1 * | 10/2001 | Heinecke et al. | .......... | 602/43 |
| 2003/0204174 A1 * | 10/2003 | Cisko, Jr. | .......... | 604/338 |
| 2006/0228318 A1 | 10/2006 | Fabo et al. | .......... | 424/443 |
| 2007/0282238 A1 * | 12/2007 | Madsen et al. | .......... | 602/48 |
| 2008/0009779 A1 | 1/2008 | Fabo et al. | .......... | 604/338 |
| 2008/0097361 A1 | 4/2008 | Fabo et al. | .......... | 604/338 |
| 2008/0281246 A1 * | 11/2008 | Effing et al. | .......... | 602/52 |
| 2009/0315317 A1 * | 12/2009 | Anderson | .......... | 283/81 |
| 2010/0063435 A1 * | 3/2010 | Hansen | .......... | 602/54 |
| 2010/0159192 A1 * | 6/2010 | Cotton | .......... | 428/137 |
| 2010/0217215 A1 * | 8/2010 | Lykke et al. | .......... | 604/344 |
| 2010/0280467 A1 * | 11/2010 | Uematsu | .......... | 604/307 |
| 2010/0307513 A1 | 12/2010 | Svensby et al. | .......... | 602/54 |
| 2010/0318013 A1 * | 12/2010 | Fabo et al. | .......... | 602/54 |
| 2012/0323193 A1 | 12/2012 | Johannison | .......... | 604/344 |

FOREIGN PATENT DOCUMENTS

| | | |
|---|---|---|
| EP | 1254647 | 11/2002 |
| SE | 1050358-9 | 4/2010 |
| WO | WO 00/61040 | 10/2000 |
| WO | WO 2006/075950 | 7/2006 |
| WO | WO 2011/129738 | 10/2011 |
| WO | WO 2011/129749 | 10/2011 |

OTHER PUBLICATIONS

Written Opinion issued on Aug. 10, 2011 for International Patent Application No. PCT/SE2011/050431, which was filed on Apr. 8, 2011 [Inventor—Uveborn; Applicant—Mölnlycke Health Care AB;] [6 pages].

International Search Report issued on Aug. 10, 2011 for International Patent Application No. PCT/SE2011/050431, which was filed on Apr. 8, 2011 [Inventor—Uveborn; Applicant—Mölnlycke Health Care AB;] [5 pages].

\* cited by examiner

OSTOMY DEVICE

CROSS-REFERENCE TO RELATED APPLICATIONS

The present application is a U.S. National Phase Application of International Application No. PCT/SE2011/050431, filed Apr. 8, 2011, which claims priority to Swedish Patent Application No. 1050358-9, filed Apr. 12, 2010, and U.S. Patent Application No. 61/322,973, filed Apr. 12, 2010, all of which applications are incorporated herein fully by this reference.

TECHNICAL FIELD

The present invention relates to a body attachment wafer for an ostomy device, and an ostomy device comprising the body attachment wafer.

BACKGROUND OF THE INVENTION

It is essential that an ostomy device stay attached to the body of the wearer in a secure way. Furthermore, such a device must be attached to the body of the wearer so that liquid or odour will not leak out to the environment surrounding the ostomy device. The skin around a stoma opening in the body is usually very sensitive so liquid from the stoma opening leaking onto the skin of the wearer has a detrimental effect on the skin. It is therefore important to ensure that the ostomy device is accurately attached to the body of the wearer.

An ostomy device typically comprises an ostomy pouch and a body attachment wafer including an adhesive layer, which is covered by a release sheet. Upon attaching the ostomy device to the body, the release sheet must be removed and the body attachment wafer is pressed against the skin of the wearer. It is desired to attach the body attachment wafer in an accurate position at the first try, since detaching the adhesive layer from the skin may damage the adhesive force of the adhesive layer, which may result in unnecessary disposal of the ostomy device.

There is thus a need for an improved body attachment wafer that allows accurate positioning of the wafer to the stoma of the wearer.

SUMMARY OF THE INVENTION

According to the present invention a body attachment wafer for an ostomy device is provided, which allows accurate positioning of the wafer to the stoma of the wearer. The body attachment wafer has a stoma opening, and an adhesive layer, said adhesive layer being covered by a release layer, having an opening which corresponds to the stoma opening. The release layer is divided along at least one dividing line from the stoma opening to the periphery of the body attachment wafer, and the release sheet includes a first grip tab extending from the release sheet in the area of the at least one dividing line, said first grip tab being arranged to overlap the release sheet on the other side of the dividing line.

The release layer preferably comprises at least a first and a second release sheet member, which meet along the dividing line across the body attachment wafer, which leads from the stoma opening to the periphery of the body attachment wafer, on each side of the stoma opening, so that each release sheet member only partially encircles the stoma opening of the body attachment wafer, and that at least the first release sheet member includes a first grip tab extending from the release sheet member in the area of the dividing line, said first grip tab being arranged to overlap the second release sheet member along the dividing line, which advantageously intersects the centre of the stoma opening. The first grip tab preferably has a length, in the direction perpendicular to the dividing line, which is at least 0.5 cm.

The second release sheet member may advantageously include a second grip tab, which is folded back, whereby the first grip tab of the first release sheet member extends over the area between the first and second release sheet members, so that it at least partially overlaps the second grip tab, said first and second grip tabs preferably having different lengths.

Preferably, at least the first release sheet member includes two grip portions provided on each side of the stoma opening, the distance between the grip portions advantageously being larger than the width of the stoma opening. This can be achieved by providing the grip portions such that they each have an inner side edge, which is at an acute angle in relation to the dividing line. When the body attachment wafer comprises a plastic film, the material of the release sheet is preferably stiffer than the plastic film.

The invention also relates to an ostomy device comprising an ostomy pouch and a body attachment wafer as described above.

DETAILED DESCRIPTION

Figure 1:
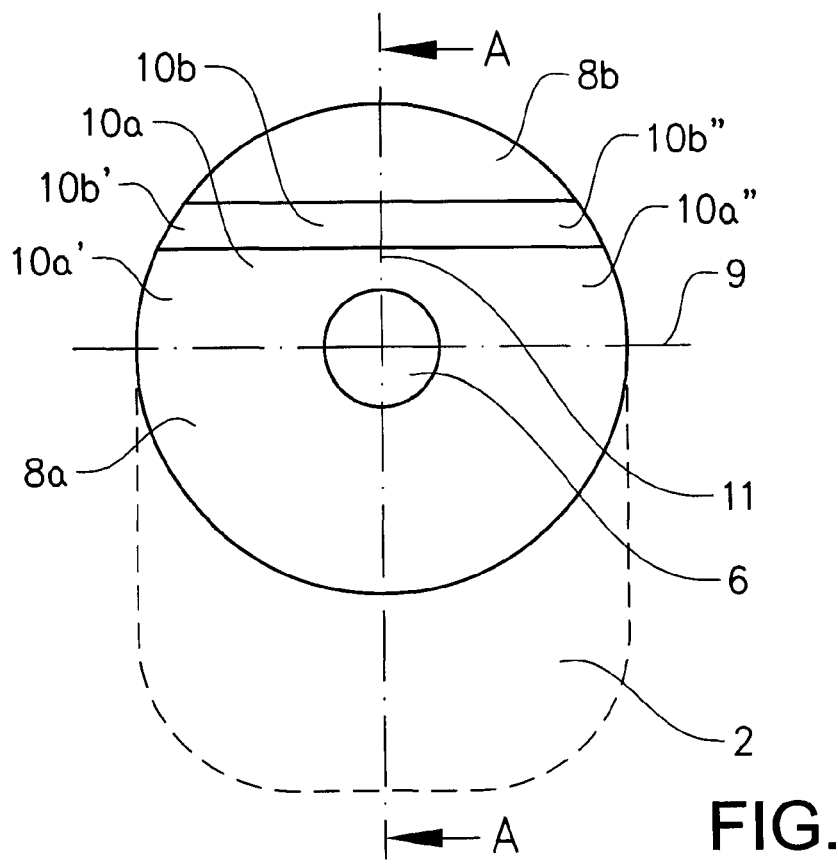
FIG. 1 is schematic top view of a body attachment wafer according to an embodiment of the invention

The present invention relates to a body attachment wafer for an ostomy device. An ostomy device comprises an ostomy pouch and a body attachment wafer, which is applied to the ostomy pouch. The body attachment wafer and the ostomy pouch may be provided as separate components to be assembled at a later stage, or may be provided attached to each other as a ready-to-use article. The body attachment wafer has an opening for the stoma and is attached to the ostomy pouch so that the stoma opening is within the area of the entrance opening of the ostomy pouch. The stoma opening of the body attachment wafer is typically smaller than the entrance opening of the ostomy pouch, so as to allow the user to cut a customized stoma opening. The body attachment wafer is to be applied to the skin around the stoma, so as to securely hold the ostomy device in place and prevent leakage, and therefore includes an adhesive layer, which is covered by a release layer, which serves to protect the adhesive layer from dirt and contaminants. Before the body attachment wafer can be attached to the skin the release layer must be removed. According to the present invention an opening corresponding to the stoma opening is provided in the release layer so that the body attachment wafer can be positioned on the stoma without removing the release layer. The release layer is divided along at least one dividing line, which leads at least from the stoma opening to the periphery of the body attachment wafer. The release sheet includes a first grip tab extending from the release sheet in the area of the dividing line so as to overlap the release sheet on the other side of the dividing line. The release layer preferably comprises at least a first and a second release sheet member, which are separate from each other, and which meet along a line across the body attachment wafer intersecting the stoma opening, i.e. the dividing line. Thereby, each release sheet member only partially encircles the stoma opening of the body attachment wafer. The dividing line between the release sheet members can be in any form as long as it leads from the stoma opening to the outer periphery of the release layer. It may be a straight line, or may be curved or serrated. Different dividing lines could be provided on each side of the stoma opening, such that the dividing line on one side of the stoma opening can be offset from, or form an angle with the dividing line on the other side. At least one of the release sheet members is provided with a grip tab, which extends from the release sheet member where it meets the other release sheet member, i.e. in the middle of the body attachment wafer, close to the stoma opening. By means of the grip tab provided close to the stoma opening, the release sheet member can easily be removed from the center of the body attachment wafer. The ostomy device can thus be held by hand over the stoma while the release sheet member is gradually removed in a direction away from the stoma, and as the adhesive layer gradually exposed it can be pressed against the skin and be attached bit by bit to the area around the stoma. By means of this centrally arranged grip tab an accurate positioning of the ostomy device can thus be ensured. The grip tab of the first release sheet member is arranged to overlap the second release sheet member along the dividing line.

It is preferred that both the first and the second release sheet member include grip tabs arranged along the dividing line, thereby facilitating the correct positioning of the entire adhesive layer of the body attachment wafer to the skin of the user. The grip tab of the second release sheet member, i.e. the second grip tab, is folded back, away from the dividing line, while the first grip tab (of the first release sheet member) extends over the dividing line so that it at least partially overlaps the second grip tab, thereby ensuring that no dirt enters the adhesive layer, and that the adhesive does not dry out.

The grip tabs preferably have a length of at least 0.5 cm, preferably 1-3 cm, to allow easy gripping of the grip tab. The grip tabs preferably have different length to allow easy gripping of the grip tabs and avoid that they cling together. The second grip tab, which is folded back and thus initially located under the first grip tab, may be longer than the first grip tab, such that it extends beyond the first grip tab, thereby exposing the outer edge of both grip tabs. The grip tabs may be provided as an integrated part of each release sheet member, or may be of a different material which is separately attached to the release sheet members.

The release sheet members are preferably shaped and arranged on the body attachment wafer such that they meet along a line, which intersects the centre of the stoma opening, the dividing line being a centre line. Thereby, each release sheet members will encircle half the periphery of the stoma opening, thus further facilitating removal of the release sheet members, since the edge of the release sheet material does not tend to get caught by the stoma. In some applications, more than two release sheet members may be contemplated, each of the preferably having a grip tab close to the stoma opening.

The grip tabs may reach over the entire width of the body attachment wafer. An opening for the stoma can be provided in the first grip tab, so that the release sheet material of the first release sheet member and the grip tab together encircle the entire stoma opening. The second grip tab has a cut out for the stoma opening, such that it does not cover the stoma opening. When applying the body attachment wafer to the stoma, the first grip tab is folded back away from the dividing line, so that the first release sheet member can be removed without getting caught by the stoma. However, it is particularly preferred that the grip tabs of one or both release sheet members each include two grip portions, which are provided on each side of the stoma opening. Thereby, the first grip tab need not be folded back before placing the body attachment wafer on the stoma, which substantially facilitates the fitting of the stoma to the ostomy device. The two grip portions can by achieved by providing a cut in the grip tab, so as to divide the grip tab into two grip portions. Preferably, there is a distance between the portions of the grip tab. When the distance between the outer ends of the grip portions is larger than the width of the stoma opening it will be easy to position the body attachment wafer over the stoma and draw the release sheet member off the body attachment wafer. The release sheet members and their grip portions are suitably shaped such that the release sheet members align half the periphery of the stoma opening, and the inner edge of the grip portion, i.e. the edge which is directed towards the stoma opening, is at an acute angle (i.e. less than 90°, preferably 30-80°) in relation to the dividing line. Accordingly, the grip portions will taper in a direction away from the dividing line, such that the distance between the stoma opening and the inner edge of the grip portion increases in the direction away from the dividing line. Thereby, the risk of the grip tab interfering with and irritating the stoma during application of the body attachment wafer is minimized, as the grip portion can be pulled sideways, in a somewhat lateral movement before pulling the release sheet members off the body attachment wafer. This solution also allows customizing the stoma opening by cutting, without impairing the grip tabs. In order to facilitate gripping of the grip tab/grip portions, each grip tab/grip portion should preferably extend at least 0.5 cm, most preferably 1-3 cm.

The release sheet material should be flexible enough to be easily folded and to enable easy removal from the body attachment wafer. The body attachment wafer may comprise a relatively stiff hydrocolloid sheet, or a very thin flexible plastic film coated with a skin friendly adhesive.

A suitable plastic film material is preferably polyurethane (PU), but other plastic materials such as polyethylene (PE) and ethylene-vinyl acetate (EVA) can also be used. The plastic film is preferably coated with a layer of soft and tacky silicone gel. Such an adhesive is skin friendly and has an excellent sealing effect. Examples of silicone gel adhesives suitable to be used as coating on the plastic film are given in WO2006/075950, which is referred to in this respect. Such silicone gel adhesives should have a softness measured as a penetration value of 20-10 mm and a weight per unit area of at least 50 g/m$^2$, whereby the weight per unit area increases with decreasing softness. The softness is measured by a method based on ASTM D 937 and described in WO2006/075950, which is referred to in this respect. Acrylate adhesives may also be used.

The plastic film of the body attachment wafer should be thin in order to ensure that the stiffness of the film will not prevent the silicone gel adhesive from penetrating into all irregularities in the skin. The plastic film should therefore have a thickness of 15-60 micrometers. The stiffness of the plastic film, expressed as bending rigidity, is preferably less than 3 mm, measured by the method as described in WO 2006/075950, preferably less than 1.8 mm.

The skin friendly adhesive is preferably a silicone gel, which has a weight per unit area greater than 50 g/m$^2$ and a penetration value greater than 10 mm.

When a plastic film is used in the body attachment wafer it is advantageous if the release layer material is stiffer than the plastic film, so that it can also serve to steady the body attachment wafer. A suitable release sheet material is preferably polyethylene (PE), polypropylene (PP) or polyurethane (PU), suitably having a thickness of 50-200 micrometers. A thin plastic film may easily become wrinkled when the release layer is removed, and is therefore more difficult to handle and to apply successfully to the skin, and is very difficult to reposition without creating wrinkles that may cause leakage. The divided release layer having central grip tabs according to the present invention is thus particularly advantageous when the body attachment wafer is a plastic film.

The body attachment wafer may be applied to the user such that the first release sheet member will be located below the stoma, and when removing the release sheet, the first release sheet member will be pulled downwards. This allows the user to see how the ostomy device is fitted on the stoma, while gradually attaching the adhesive body attachment wafer to the skin below the stoma. When the lower part of the body attachment wafer is accurately applied to the skin, the upper part of the body attachment wafer is removed in a similar way by pulling the second release sheet member upwards.

Figure 2:
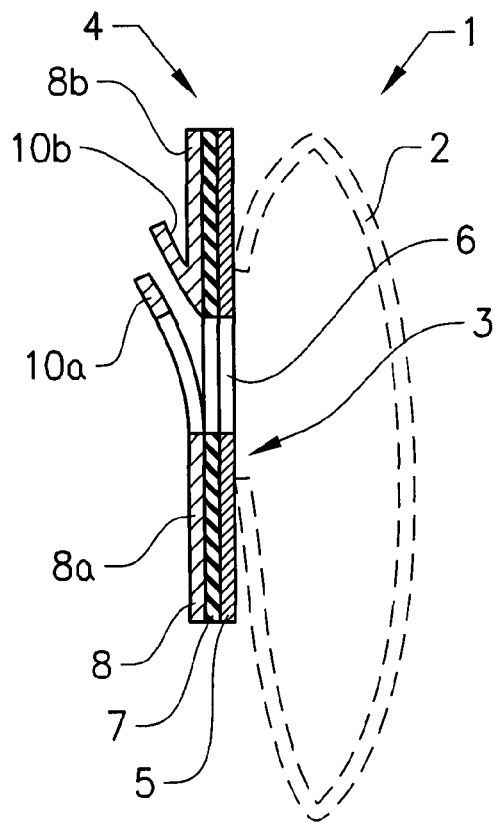
FIG. 2 is a cross-sectional view of the body attachment wafer shown in FIG. 1.
Figure 3:
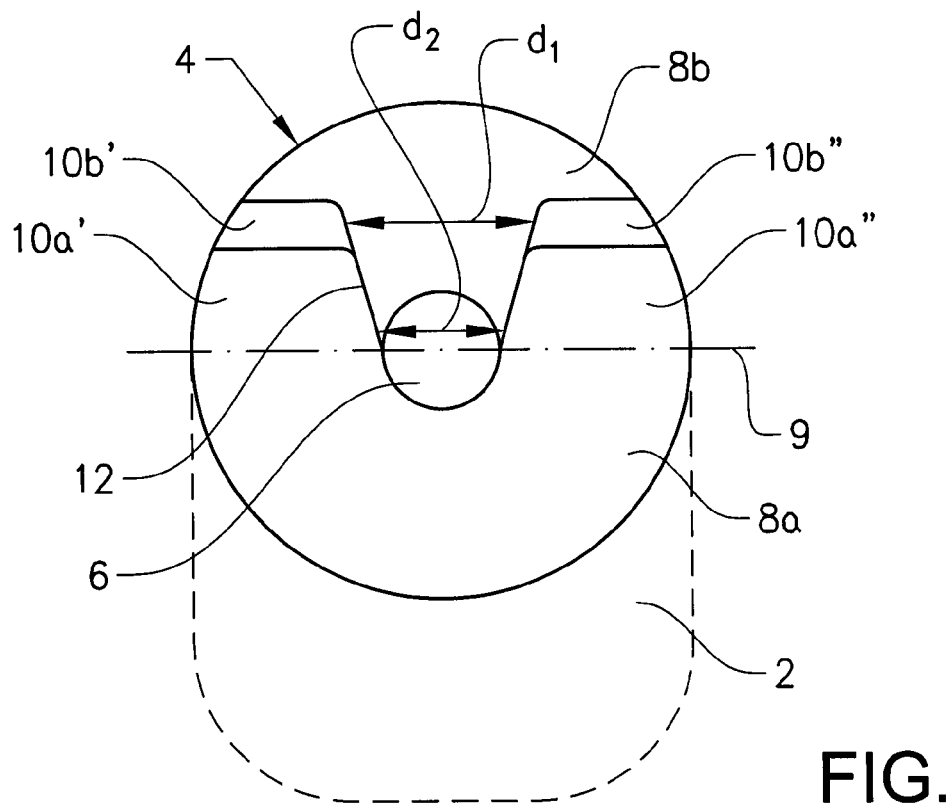
FIG. 3 is schematic top view of a body attachment wafer according to another embodiment of the invention.

FIGS. 1-4 show some illustrative embodiments of the invention. In the drawings the same reference numbers are use for corresponding elements, although these may have a somewhat different design in different embodiments of the invention. FIG. 1 shows an ostomy device (1) comprising a body attachment wafer (4) according to an embodiment of the invention, and FIG. 2 shows a cross-sectional view along the line A-A of FIG. 1. The body attachment wafer (4) is applied to an ostomy pouch (2) (shown in dashed line, as it is not part of the body attachment wafer) having an entrance opening (3). The body attachment wafer (4) includes a plastic film (5), which has a stoma opening (6), and is coated with a skin friendly adhesive (7) on the side thereof, which is distal to the ostomy pouch (2). The adhesive layer (7) is covered by a release layer (8), and an opening corresponding to the stoma opening (6) is provided in the release layer (8). The release layer (8) comprises a first sheet member (8a) and a second release sheet member (8b), which meet along a dividing line (9). In this embodiment the dividing line (9) intersects the centre of stoma opening. Each release sheet member encircles the stoma opening (6) only partially.

The first release sheet member (8a) includes a first grip tab (10a) extending from the release sheet member upwards in FIGS. 1 and 2. The first grip tab (10a) is thus arranged to overlap the second release sheet member (8b) along the dividing line (9). The second release sheet member (8b) includes a second grip tab (10b), which is folded back (upwards in FIG. 1), and the first grip tab (10a) of the first release sheet member (8a) extends over the area between the first and second release sheet members, so that it overlaps the second grip tab (10b). The second grip tab (10b) is longer than the first grip tab (10a), such that the second grip tab extends beyond the first grip tab. Both release sheet members (8a, 8b) include two grip portions (10a', 10a"; 10b', 10b"), which are provided on each side of the stoma opening. In the embodiment shown in FIG. 2, the grip tabs (10a, 10b) have a width that corresponds to the full width of the release layer, and the grip portions are provided by means of a cut (11) in the grip tab in the area above the stoma opening. In the embodiment shown in FIG. 3, the grip portions have inner side edges (12), which each are at an acute angle in relation to the line (9), such that the distance ($d_1$) between the grip portions is larger than the width ($d_2$) of the stoma opening. This allows the grip tab portions (10a', 10a") to be pulled sideways, in a somewhat lateral movement before pulling the release sheet members (8a, 8b) off the body attachment wafer. The body attachment wafer shown in FIG. 1-4 is circular, but could have any desired shape.

Figure 4:
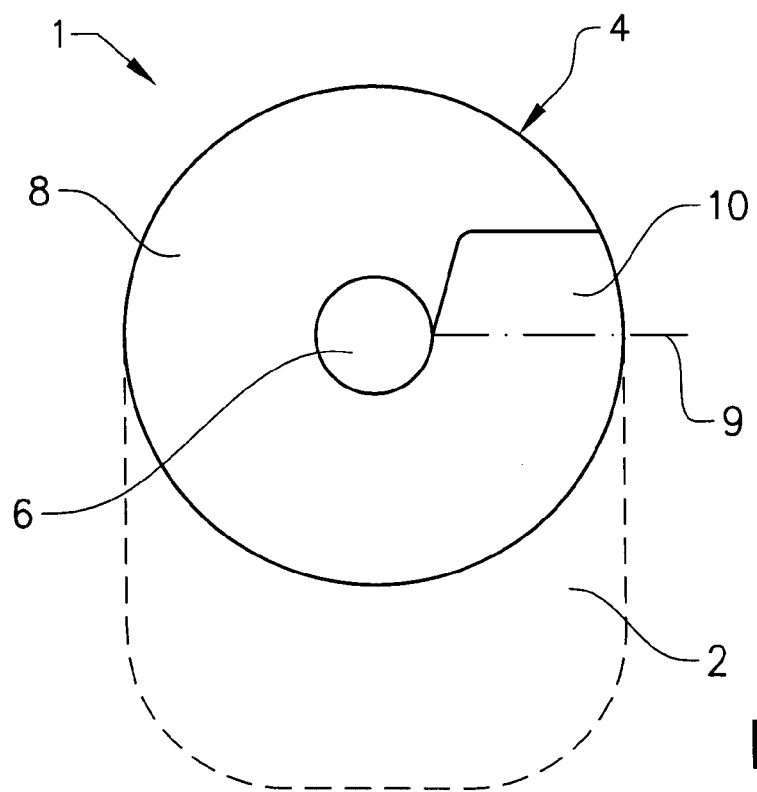
FIG. 4 is schematic top view of a body attachment wafer according to yet another embodiment of the invention.

FIG. 4 shows an embodiment of the body attachment wafer (4) having a dividing line (9) only on one side of the stoma opening (6). The release layer (8) is in one part and includes a grip tab (10) overlapping the release layer on the other side of the dividing line. In this embodiment no grip tab is needed on the edge of the release layer on the other side of the dividing line.

The invention claimed is:

1. A body attachment wafer for an ostomy device, comprising:
an adhesive layer defining a stoma opening; and
a release layer having an opening which is at least partially aligned with the stoma opening, wherein at least a portion of the release layer is configured to cover the adhesive layer,
wherein the release layer is divided along a dividing line extending from the stoma opening to a periphery of the body attachment wafer on opposing sides of the stoma opening, wherein the dividing line divides the release layer into a first part and a second part,
wherein the release layer comprises at least a first member that comprises two grip portions provided on opposing sides of the stoma opening, wherein each of the two grip portions of the first member has an inner side edge, wherein a portion of the first member is releasably attached to the adhesive layer in the first part, and wherein the grip portions extend away from the adhesive layer and are arranged to overlap the release layer on the second part, and wherein a distance between the inner side edges of the two grip portions of the first member is greater than a width of the stoma opening.

2. The body attachment wafer of claim 1, wherein each of the inner side edges of the two grip portions of the first member is at an acute angle in relation to the dividing line.

3. The body attachment wafer of claim 1, wherein the release layer comprises a second member that meets the first member along the dividing line such that each of the first and second members only partially encircles the stoma opening of the body attachment wafer, and wherein a portion of the second member is releasably attached to the adhesive layer in the second part.

4. The body attachment wafer of claim 3, wherein the second member comprises two grip portions provided on opposing sides of the stoma opening, wherein each of the two grip portions of the second member has an inner side edge, wherein the second member grip portions extend away from the adhesive layer in the area of the dividing line, wherein a distance between the inner side edges of the two grip portions of the second member is greater than the width of the stoma opening.

5. The body attachment wafer of claim 4, each of the inner side edges of the two grip portions of the second member is at an acute angle in relation to the dividing line.

6. The body attachment wafer of claim 4, wherein the second member grip portions are folded back, and wherein the first member grip portions at least partially overlap the second release grip portions.

7. The body attachment wafer of claim 4, wherein the first member grip portions and the second member grip portions have different lengths.

8. The body attachment wafer of claim 7, wherein the second member grip portions are longer than the first member grip portions.

9. The body attachment wafer of claim 4, wherein the first member grip portions are arranged to overlap the second member over the second part of the release layer.

10. The body attachment wafer of claim 1, wherein the dividing line intersects the center of the stoma opening.

11. The body attachment wafer of claim 1, wherein the first member grip portions have a length of at least 0.5 cm in the direction perpendicular to the dividing line.

12. The body attachment wafer of claim 1, further comprising a plastic film on the side of the adhesive layer opposite to the release layer, wherein the release layer is stiffer than the plastic film.

13. An ostomy device comprising an ostomy pouch having an entrance opening and a body attachment wafer of claim 1.

\* \* \* \* \*